United States Patent [19]

Klingelhöller

[11] Patent Number: 5,798,341
[45] Date of Patent: Aug. 25, 1998

[54] USE OF COBALAMINS FOR TOPICAL TREATMENT OF SKIN DISORDERS

[76] Inventor: Karsten Klingelhöller, Eintrachtstrasse 39, 42275 Wuppertal, Germany

[21] Appl. No.: 553,542
[22] PCT Filed: Jun. 15, 1994
[86] PCT No.: PCT/EP94/01951
§ 371 Date: Mar. 25, 1996
§ 102(e) Date: Mar. 25, 1996
[87] PCT Pub. No.: WO94/28907
PCT Pub. Date: Dec. 22, 1994

[30] Foreign Application Priority Data

Jun. 15, 1993 [DE] Germany ............ 43 19 629.2

[51] Int. Cl.$^6$ ............ A61K 31/70
[52] U.S. Cl. ............ 514/52
[58] Field of Search ............ 514/52

[56] References Cited

U.S. PATENT DOCUMENTS

3,548,057 12/1970 Kelley et al.
3,577,537 5/1971 Howe.

FOREIGN PATENT DOCUMENTS

| 0055118 | 6/1982 | European Pat. Off. |
| 1922192 | 12/1969 | Germany. |
| 2325809 | 12/1974 | Germany. |
| 2505114 | 8/1976 | Germany. |
| 3210669 | 9/1983 | Germany. |
| 2413252 | 6/1994 | WIPO. |

OTHER PUBLICATIONS

Embase Abstract 91098487, Grimalt et al. (1990).
Embase Abstract 77016917, Feiwel (1976).
J. Nutr., 92(2), Jun. 1967, pp. 261–266: E.E. Howe et al. "Percutaneous Absorption of Vitamin B12 in the Rat and Guinea Pig".
"Vitamin Compendium" 1976, Vitamins and Chemicals Department, F. Hoffman–La Roche & Co. Ltd., Basle Switzerland, pp. 110–115.
Chemical Abstracts, vol. 88, No. 11, Mar. 13, 1978, Columbus, Ohio: abstract No. 72417f, R.G.Gadzhiev et al. "Status of blood electrolytes in patients with allergic dermatitis".

86–052836/08 On Corp, Jun. 21, 1984–JP–128199 (Jan. 13, 1986) A61k–07, Derwent "Cellular function activating agent—for skin activation and acceleration of hair growth".

*Primary Examiner*—Zohreh Fay
*Attorney, Agent, or Firm*—Friedrich Kueffner

[57] ABSTRACT

Use of compounds of the Formula

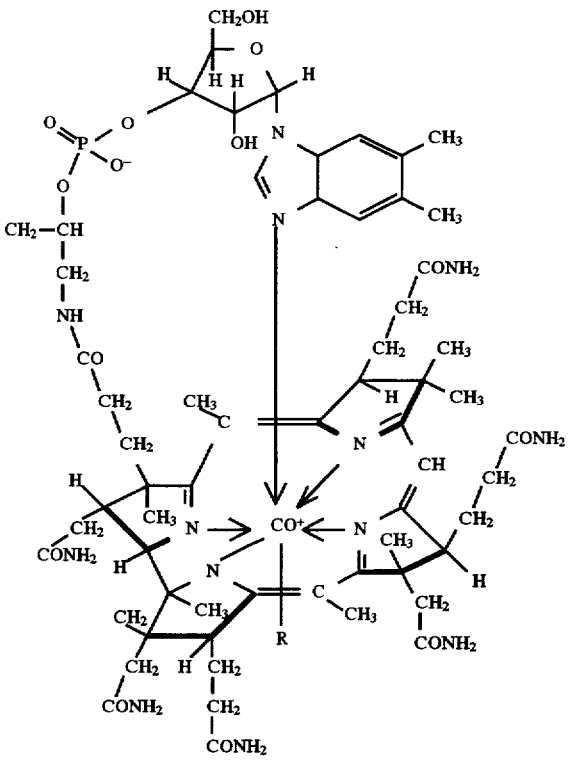

in which

R stands for CN, OH, $CH_3$ or $H_2O$ for topical treatment of skin diseases and hair growth disturbances as well as a pharmaceutical formulation containing, in addition to standard carrier and/or dilution substances, compounds in accordance with Formula I as defined in claim 1 and a synthetic or vegetable-based oil or fat.

3 Claims, No Drawings

USE OF COBALAMINS FOR TOPICAL TREATMENT OF SKIN DISORDERS

This application is a 371 of PCT/EP94/01951 filed Jun. 15, 1994 published as WO94/28907 Dec. 22, 1994.

The invention pertains to a new use of cobalamins for topical treatment of skin disorders and in particular of inflammatory and hyperproliferative skin disorders and/or cutaneous manifestations of illnesses which are immunologic in origin, e.g. psoriasis, atopic dermatitis, contact dermatitis and other eczematous dermatitises, seborrhoeic dermatitis, neurodermatitis, decubitus, lichen planus, pemphigus, bullate pemphigoid, epidermolysis bullosa, urticaria, angioedemas, vasculitides, erythema, cutaneous eosinophilias, lupus erythematosus as well as alopecia areata and hair growth disturbances.

The treatment of skin disorders and in particular of chronic skin disorders poses a great problem in medicine since they are curable only to a very limited extent. The treatment of these ailments in many cases provides only minor relief to the patients; in many cases no healing success at all can be observed. In addition, a large number of the active ingredients utilized, such as cortisone, exhibit powerful side effects.

The object of the present invention is to make available an effective substance for the treatment of skin disorders and particularly those listed above, and which if possible exhibits no side effects whatsoever.

Surprisingly, it was found that compounds characterized by Formula I,

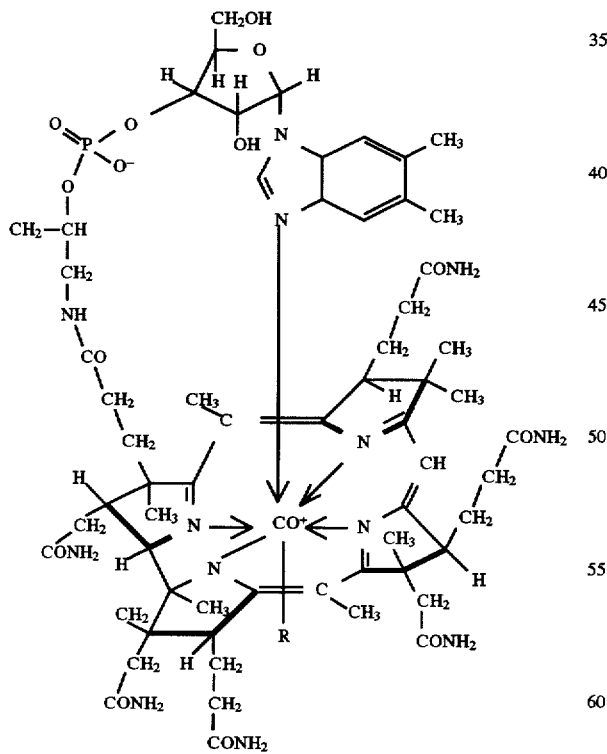

in which
R stands for CN, OH, CH$_3$ or H$_2$O, exhibit nothing other than excellent results in topical treatment of skin disorders and in particular of inflammatory and hyperproliferative skin ailments and/or cutaneous manifestations of illnesses which are immunologic in origin, e.g. psoriasis, atopic dermatitis, contact dermatitis and other eczematous dermatitises, seborrhoeic dermatitis, neurodermatitis, decubitus, lichen planus, pemphigus, bullate pemphigoid, epidermolysis bullosa, urticaria, angioedemas, vasculitides, erythema, cutaneous eosinophilias, lupus erythematosus as well as alopecia areata and hair growth disturbances.

The compounds characterized by Formula I are also known under the designation cobalamine or vitamin B$_{12}$. They are administered in medicine orally or subcutaneously in the form of tablets or injection solutions for example to treat pernicious anemia.

The dosage to be administered for the above application will depend on the compound selected, the method of administration and the treatment method. Very good results are achieved where one or more compounds as per Formula I are applied locally one or more times daily at a concentration of from $1 \times 10^{-4}$ to $1 \times 10^{-2}$ percent by weight. The presentations may contain carrier and dilution substances commonly used in the pharmaceuticals industry. Examples of suitable galenic forms are solutions, emulsions, suspensions, lotions, gels, ointments or creams.

The compounds characterized by Formula I are preferably applied in combination with a synthetic or natural oil. The use of vegetable oils and in particular of almond oil, peanut oil, sesame oil, olive oil, wheat germ oil, maize germ oil, thistle oil, soy oil, sunflower oil, coconut oil, avocado oil, palm oil and cocoa butter has proven to be particularly suitable.

A further subject of the present invention is a pharmaceutical formulation containing compounds characterized by Formula I and a vegetable oil or fat.

The effects of the compounds characterized by Formula I can be seen from the following trials:

EXAMPLES

Making up an ointment: 350 ml of avocado oil, 350 ml of distilled water, 70 ml of D-Panthenol, 525 mg of cyanocobalamin, 175 mg of hydroxocobalamin and 100 g of emulsifier, e.g. available under the trade names Euxyl K, Lame-creme or Emulsan, mixed and then topped up to 1000 ml.

Example 1

Effect on psoriasis

In a group of ten test subjects suffering from psoriasis, the ointment made up as above was applied three times daily to the afflicted skin area. The effect of the ointment proposed by way of invention on the diseased skin was observed for an area of skin measuring 10 cm$^2$.

| Days applied | Afflicted skin area, cm$^2$ |
| --- | --- |
| 1 | 10 |
| 5 | 9 |
| 10 | 8 |
| 20 | 4 |

-continued

| Days applied | Afflicted skin area, cm² |
|---|---|
| 25 | 2 |
| 30 | 0 |

Example 2

Effect on neurodermatitis

As in example 1, in a group of ten test subjects suffering from neurodermatitis the ointment made up as above was applied three times daily to the afflicted skin areas. The effect of the ointment in accordance with the invention on the afflicted skin was observed for an area of skin measuring 10 cm².

| Days applied | Afflicted skin area, cm² |
|---|---|
| 1 | 10 |
| 5 | 8 |
| 10 | 6 |
| 20 | 4 |
| 25 | 2 |
| 30 | 0 |

The above examples make it evident that the use, in accordance with the invention, of compounds characterized by Formula I not only will provide relief but will also reduce the size of the afflicted skin areas to an area of as little as 0 cm² within a relatively short period of time.

I claim:

1. A method of carrying out a topical treatment of inflammatory and hyperproliferative skin elements and/or cutaneous manifestations of illnesses which are immunologic in origin, the method comprising using compounds having the formula

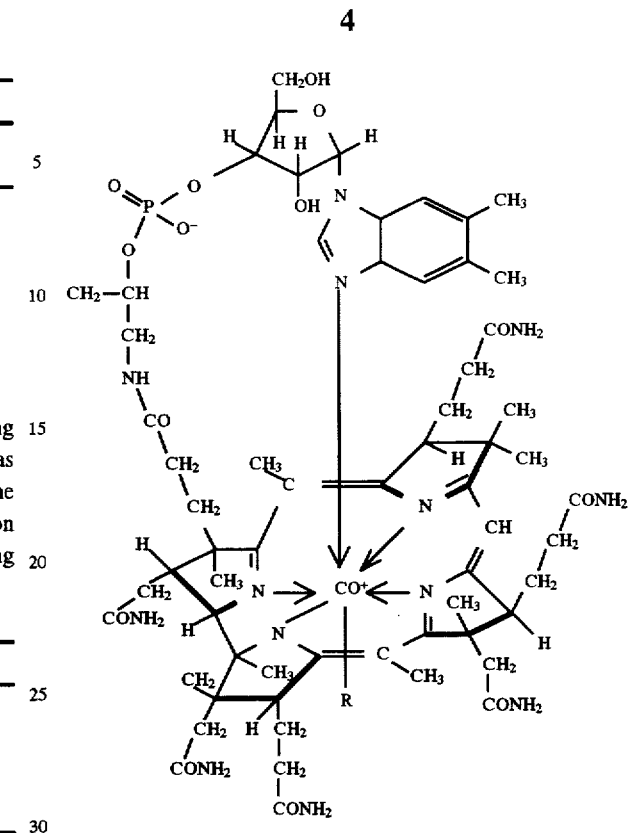

wherein R is selected from the group consisting of CN, OH, $CH_3$ and $H_2O$.

2. The method according to claim 1, wherein the inflammatory and hyperproliferative skin ailments and/or cutaneous manifestations of illnesses which are immunologic in origin are psoriasis, atopic dermatitis, contact dermatitis and other eczematous dermatitises, seborrhoeic dermatitis, neurodermatitis, decubitus, lichen planus, pemphigus, bullate pemphigoid, epidermolysis bullosa, urticaria, angioedemas, vasculitides, erythema, cutaneous eosinophilias, lupus erythematosus as well as alopecia areata and hair growth disturbances.

3. The method according to claim 1, comprising using conventional carrier substances and/or delusions.

* * * * *